United States Patent
Kilsgaard et al.

(10) Patent No.: US 9,808,199 B2
(45) Date of Patent: Nov. 7, 2017

(54) TWO PART EEG MONITOR WITH DATABUS AND METHOD OF COMMUNICATING BETWEEN THE PARTS

(75) Inventors: Soren Kilsgaard, Smorum (DK); Preben Kidmose, Maarslet (DK); Mike Lind Rank, Farum (DK)

(73) Assignee: Widex A/S, Lynge (DK)

( * ) Notice: Subject to any disclaimer, the term of this patent is extended or adjusted under 35 U.S.C. 154(b) by 717 days.

(21) Appl. No.: 13/588,483

(22) Filed: Aug. 17, 2012

(65) Prior Publication Data

US 2012/0316418 A1 Dec. 13, 2012

Related U.S. Application Data

(63) Continuation-in-part of application No. PCT/EP2011/053518, filed on Mar. 9, 2011, and a
(Continued)

(51) Int. Cl.
*A61B 5/0476* (2006.01)
*A61B 5/0478* (2006.01)
(Continued)

(52) U.S. Cl.
CPC .......... *A61B 5/6817* (2013.01); *A61B 5/0476* (2013.01); *A61B 5/0478* (2013.01);
(Continued)

(58) Field of Classification Search
CPC ... A61B 5/0478; A61B 5/0476; A61B 5/6802; A61B 5/6815; A61B 5/6817;
(Continued)

(56) References Cited

U.S. PATENT DOCUMENTS

| 4,198,621 A | 4/1980 | Roper |
| 5,773,791 A | 6/1998 | Kuykendal |
(Continued)

FOREIGN PATENT DOCUMENTS

| EP | 1671578 A1 | 6/2006 |
| JP | 2006-102260 A | 4/2006 |
(Continued)

OTHER PUBLICATIONS

Awtrey "Transmitting Data and Power over a One-Wire Bus" Sensors Magazine (1997) (retrieved Jun. 23, 2015).*
(Continued)

*Primary Examiner* — Lee S Cohen
*Assistant Examiner* — Erin M Cardinal
(74) *Attorney, Agent, or Firm* — Sughrue Mion, PLLC

(57) ABSTRACT

A personal wearable EEG monitor comprises a base part (1) having signal processing means (23), and an electrode part (2) with at least two electrodes (11, 12) for measuring an EEG signal of a person. The electrode part (2) comprises means for converting the EEG signal into a digital signal. The EEG monitor comprises a databus for transferring data between the base part (1) and the electrode part (2) and for providing power from one part to the other. The databus is adapted for application of two electrical wires. The invention further provides a method for communicating between two parts of an EEG monitor.

28 Claims, 6 Drawing Sheets

Related U.S. Application Data continuation-in-part of application No. PCT/EP2010/052960, filed on Mar. 9, 2010.

(51) Int. Cl.
*A61B 5/00* (2006.01)
*G06F 1/26* (2006.01)
*H04R 25/00* (2006.01)
H04B 3/54 (2006.01)
H02J 7/34 (2006.01)

(52) U.S. Cl.
CPC ............ *A61B 5/6815* (2013.01); *G06F 1/266* (2013.01); *H04R 25/60* (2013.01); *A61B 2560/0214* (2013.01); *A61B 2560/0219* (2013.01); *H02J 7/345* (2013.01); *H04B 3/542* (2013.01); *H04R 2225/021* (2013.01); *H04R 2460/03* (2013.01)

(58) Field of Classification Search
CPC .......... A61B 5/6814; A61B 2560/0214; A61B 2560/0219; H04R 25/60; H04R 2460/03
USPC ........ 600/372, 373, 379, 383, 393, 544–545
See application file for complete search history.

(56) References Cited

U.S. PATENT DOCUMENTS

| | | | |
|---|---|---|---|
| 5,774,791 A | 6/1998 | Strohallen et al. | |
| 5,878,146 A | 3/1999 | Andersen | |
| 7,057,496 B2 | 6/2006 | Bateman et al. | |
| 7,286,058 B1 | 10/2007 | Gologorsky | |
| 8,842,863 B2 * | 9/2014 | Nielsen | H04R 25/407 381/322 |
| 2002/0186155 A1* | 12/2002 | Olson et al. | 341/143 |
| 2004/0116151 A1 | 6/2004 | Bosch et al. | |
| 2005/0059870 A1* | 3/2005 | Aceti | A61B 5/0002 600/340 |
| 2005/0209516 A1* | 9/2005 | Fraden | A61B 5/02055 600/323 |
| 2005/0215916 A1 | 9/2005 | Fadem et al. | |
| 2006/0149330 A1 | 7/2006 | Mann et al. | |
| 2007/0112277 A1 | 5/2007 | Fischer et al. | |
| 2007/0120715 A1 | 5/2007 | Zierhofer | |
| 2007/0269065 A1* | 11/2007 | Kilsgaard | 381/315 |
| 2009/0262964 A1 | 10/2009 | Havenith et al. | |
| 2009/0281435 A1* | 11/2009 | Ahmed | A61B 5/02416 600/502 |
| 2010/0217100 A1* | 8/2010 | LeBoeuf et al. | 600/301 |
| 2012/0039497 A1* | 2/2012 | Nielsen et al. | 381/323 |
| 2013/0035578 A1* | 2/2013 | Chiu et al. | 600/379 |

FOREIGN PATENT DOCUMENTS

| | | |
|---|---|---|
| WO | 2005076664 A1 | 8/2005 |
| WO | 2006047874 A1 | 5/2006 |
| WO | 2006066577 A1 | 6/2006 |
| WO | 2007047667 A2 | 4/2007 |
| WO | 2009100654 A1 | 8/2009 |

OTHER PUBLICATIONS

Maxim Integrated "Single-Wire Serial Bus Carries Isolated Power and Data" (2006).*
Wu et al. "A Novel Power Line Communication Technique Based on Power Electronics Circuit Topology" Applied Power Electronics Conference and Exposition (APEC), 2010 Twenty-Fifth Annual IEEE pp. 681-685 (Feb. 2010).*
Wu et al. "Power/signal time division multiplexing technique based on power electronic circuits" Applied Power Electronics Conference and Exposition (APEC), 2011 Twenty-Sixth Annual IEEE pp. 1710-1714 (Mar. 2011).*
Amtel "AVR318: Dallas 1-Wire Master" Amtel Coproration (2004).*
Wu, et al. "Power/Signal Time Division Multiplexing Technique based on Power Electronic Circuits," Applied Power Electronics Conference and Exposition (APEC), 2011 26th Annual IEEE; pp. 1710-1714 (2011).*
Office Action for counterpart Japanese Patent Application No. 2012-556500 dated Jan. 7, 2014, with English translation.
International Search Report with Written Opinion for PCT/EP2011/053518 dated Jul. 14, 2011.
Communication dated Jul. 27, 2015 issued by the European Intellectual Property Office in counterpart European Application No. 11707412.0.

* cited by examiner

TWO PART EEG MONITOR WITH DATABUS AND METHOD OF COMMUNICATING BETWEEN THE PARTS

RELATED APPLICATIONS

The present application is a continuation-in-part of application PCT/EP2011053518, filed on Mar. 9, 2011, in Europe and published as WO 2011/110582 A1. The present application is a continuation-in-part of application PCT/EP2010/052960, filed on Mar. 9, 2010, in Europe and published as WO 2011/110218 A1.

BACKGROUND OF THE INVENTION

1. Field of the Invention

The present invention relates to EEG monitors. The invention further relates to an EEG monitor in two parts connected with electrical wires. The invention more specifically concerns an EEG monitor comprising power supply means. The invention further relates to a method for communicating between two parts of an EEG monitor.

EEG is the commonly used abbreviation for Electro Encephalo-Gram, which is generally speaking a method of electrically monitoring brain activity of a person. Systems for monitoring EEGs have been known for many years. However with the general technological development, EEG monitoring systems, which may be carried or worn continuously by a person to be monitored, have been devised.

It is known to measure EEG by placing electrodes on the scalp of a person, and to record and analyse the EEG signal for various diagnostic purposes.

2. The Prior Art

A system for such a use is known from WO-A1-2006/047874, which describes measurement of brain waves by use of electrodes placed in connection with at least one of the ears of the subject, i.e. placed on an outer ear part or placed in the ear canal. The measurements are used particularly for detecting the onset of an epileptic seizure. WO-A1-2006/047874 also describes the use of electrodes in pairs as detection and reference electrodes respectively, such a setup being well known in the field of electroencephalography.

EEG monitors may also be applied for surveillance of persons having diabetes, where blood sugar levels are monitored in order to warn against hypoglycemic attacks caused by low blood sugar levels. Hypoglycaemic attacks may lead to unconsciousness and even death. A system for such surveillance of an eminent hypoglycaemic attack is disclosed in WO-A-2006/066577. This is, however, an implanted subcutaneous system.

WO-A1-2007/047667 describes an ear plug for measuring EEG-signals. The ear plug comprises an exterior shell with electrodes, the shell being made of a soft, compressible material. The signals obtained with the ear plug are transmitted to external units for processing and monitoring.

Typically, a personal EEG monitor will be made in two parts as mentioned above, i.e. a base part with signal processing means and an electrode part with at least two electrodes for measuring the EEG signal of a person. Preferably the electrode part will be made as small as possible, such that it is easily attached to the skin surface on the head of the person. The base part often comprises the power supply means, and is therefore larger. The base part would typically be arranged in a less visible position. The two parts will be connected through wires. The electrodes for measuring the EEG signal are often prepared to be arranged with skin contact in the ear region of a person. The electrodes may also be capacitive.

Since the electrode part is adapted for being arranged at or in the ear or ear region of a person, it will often comprise a receiver or speaker applied for giving sound or voice messages to the user. This could be warnings about an imminent hypoglycemic seizure. But the receiver may be applied for any type of sounds.

The electrode part could also be applied for other types of transducers. Examples of such transducers in the electrode part could be a microphone for transforming sounds into electrical signals, or a temperature sensor or an accelerometer. Also other transducers could be considered relevant to arrange in the electrode part. The electrical signal from such a transducer needs to be transferred to the signal processing means of the base part of the EEG monitor, normally by an extra pair of wires, for further processing, logging or transmission to a remote device.

One problem in having such a transducer, e.g. a microphone, is that the wires used for transferring the signal from the transducer to the base part may pick up electromagnetic interference. The electrical signal generated in e.g. a microphone may be relatively weak, e.g. 1-5 µV, and therefore rather sensitive to noise.

This problem is larger when a receiver is arranged in the electrode part, since the wires supplying the receiver signal, which may be 2 V at peak level, will be arranged close to the wires transferring the signal from the EEG electrodes and e.g. from a transducer. Therefore, there may be a risk that the receiver signal will induce noise into the wires carrying the EEG signal and any transducer signal.

US-A1-2004/0116151 describes a databus which can be applied for a hearing aid between a base part and a peripheral component. This databus is described as needing transfer of power, clock and synchronization signal.

One problem is that the number of wires should be as low as possible in order to keep the total diameter of the bundle of wires connecting the two parts as small as possible. Each wire is connected both to the electrode part and to the base part, e.g. through a connector. This connection will take up some space, and will in general be a weak point in the construction, i.e. there is a risk of losing the electrical connection at this point. Furthermore the connectors typically applied are relatively expensive components. Therefore, keeping the necessary number of connections to a minimum is to be preferred.

SUMMARY OF THE INVENTION

In a first aspect, the invention provides a personal EEG monitor with power supply means, said EEG monitor comprising a base part having signal processing means, an electrode part with at least two electrodes for measuring an EEG signal of a person, said electrode part having means for converting the EEG signal into a digital signal, and a databus for transferring data between said base part and said electrode part and for providing power from one part to the other, said databus being adapted for application of two electrical wires.

A databus is here understood to be a digital communication line which can be set up for communication between different units, suitable for carrying signals in one or two directions. The databus is a serial databus, and is here also understood to be able to transfer power.

A transducer is here understood as a device which can transfer a physical parameter into an electrical signal in the EEG monitor. This definition includes an electrode being able to read a voltage potential, such that the potential in some form can be transferred to the signal processing means of the EEG monitor.

The electrodes may be prepared for arrangement with skin contact, e.g. in the ear region of the person. The electrode may also be of the capacitive type where an EEG signal can be detected without a direct electrical contact to the skin.

In an embodiment of the EEG monitor, at least two different states of the databus are applied in different time slots, where a first state is for transfer of power and a second state is for transmission of signal from said electrode part to said base part.

In an embodiment of the EEG monitor, at least three different states of the databus are applied in different time slots, where a first state is for transfer of power, a second state is for transmission of signal from said base part to said electrode part, and a third state is for transmission of signal from said electrode part to said base part. This embodiment will often be preferred when a receiver or speaker, e.g. for providing sound messages to the person wearing the EEG monitor, is applied.

When separating in time the power transfer from the data transfer the risk of noise problems is reduced. The term different time slots refers to this separation in time of power transfer and data or signal transfer in both directions. At the same time the invention facilitates a two wire databus without the need of any further electrical wires.

In a second aspect, the invention provides a personal EEG monitor with power supply means, said EEG monitor comprising a base part having signal processing means, an electrode part with at least two electrodes for measuring an EEG signal of a person, said electrode part having means for converting the EEG signal into a digital signal, and a databus for transferring data between said base part and said electrode part and for providing power from one part to the other, said databus being adapted for application of two electrical wires; and for the application of at least four different states in respective time slots, where a first state is for transfer of power, a second state is for transmission of signal from said base part to said electrode part, a third state is for transmission of signal from said electrode part to said base part; and a fourth state set to low in order for the first state to start with a rising edge.

In an embodiment of the EEG monitor, a fourth state is added which is set to low, i.e. to "0", in order for the first state for power transfer to start with a rising edge. Such a rising edge occurring at a known place in the sequence is important in order to interpret the signal on the databus.

In an embodiment of the EEG monitor, the power supply is arranged in the base part and a capacitor is arranged in the electrode part, said capacitor adapted for being charged during said first state for transfer of power, and supplying power in periods where no power is transmitted through the databus. There will typically be more space in the base part and therefore more room for power supply, such as a battery.

In an embodiment of the EEG monitor, the first state for transfer of power takes up at least 50%, preferably at least 70%, of the time on the databus. This has been found to result in a sufficiently small power loss and a not too large capacitor for supplying power in the rest of the time.

In an embodiment of the EEG monitor where a receiver is arranged in the electrode part, the receiver is connected such that it will not draw any power in the time where data is transferred on the databus, but only in the time where power is transferred. This can be achieved by short-circuiting the receiver during the transfer of data. The advantage of this will be that the receiver will not need to draw power from a capacitor in the electrode part during the time where there is no transfer of power from the base part. This means that the capacitor in the electrode part can be made much smaller, since it will only need to supply power to the electronic circuit of the electrode part. A smaller capacitor will also have smaller physical dimensions, whereby the electrode part can be made smaller. There are possible variations of this embodiment, e.g. where the receiver draws power in a smaller part of the time where data is transferred.

In an embodiment of the EEG monitor, the electrode part comprises an electronic chip, i.e. an integrated circuit (IC), connected with the transducer, the chip or IC being connected with the databus. The chip is a space efficient way of collecting the necessary circuits, e.g. for handling the databus communication and power transfer. One circuit is a voltage regulator for the power supply. Another circuit is an analogue to digital converter for converting an analogue signal from the EEG electrodes and any other transducer into a digital signal. This analogue to digital converter is often a sigma-delta converter.

In an embodiment of the EEG monitor, a clock frequency generator is arranged in either the base part or in the electrode part of the EEG monitor, and wherein a clock frequency is regenerated, by a clock frequency regenerator in the part of the EEG monitor without clock frequency generator. Preferably, this regenerated clock frequency is synchronized with the clock frequency of said clock frequency generator. Usually the clock frequency generator is arranged in the base part of the EEG monitor, and often the synchronization is performed by a phase-locked loop.

In an embodiment of the EEG monitor, the electrode part is an ear canal plug comprising at least two electrodes on an external surface, said electrodes being arranged for having contact with the ear canal of the user in order to be able to detect electrical potentials from the person being EEG monitored.

In an embodiment of the EEG monitor, the electrode part is connected with a transducer for measuring a physical or physiological parameter. Such a transducer could be adapted for measuring temperature, blood pressure, movement e.g. acceleration, orientation, i.e. whether the person is lying down. Preferably such transducer is connected to the electronic module of the electrode part and is prepared for transferring data to the signal processing means in said base part through the serial databus. When the electrode part is arranged as an ear plug, an appropriate transducer for detecting the correct placement of the ear plug in the ear canal could also be applied. This could be a capacitive transducer.

In a third aspect, the invention provides a method for communicating between two parts of an EEG monitor comprising power supply means, comprising the steps of arranging a base part outside the ear canal of a user, said base part having signal processing means, arranging an electrode part in the ear canal of a person to be monitored, said electrode part having EEG electrodes, connecting said electrode part with said base part through a databus comprising two electrical wires adapted for transmission of signal to said receiver, and for transmission of signal from said transducer to said base part, said databus being adapted for providing power supply either from the base part to the electrode part, or, from the electrode part to the base part, through said two electrical wires, and applying at least two different states of the two wire databus sequentially in different time spans, where a first state is for transfer of power, and a second state is for transmission of signal from said electrode part to said base part.

In an embodiment of the method for communicating between two parts, at least three different states of the two wire databus are applied sequentially in different time spans, where a first state is for transfer of power, a second state is for transmission of signal from the base part to the electrode part, and a third state is for transmission of signal from the electrode part to the base part.

BRIEF DESCRIPTION OF THE DRAWINGS

Embodiments of the invention will now be explained in further detail with reference to the figures.

DETAILED DESCRIPTION OF THE INVENTION

Figure 1:
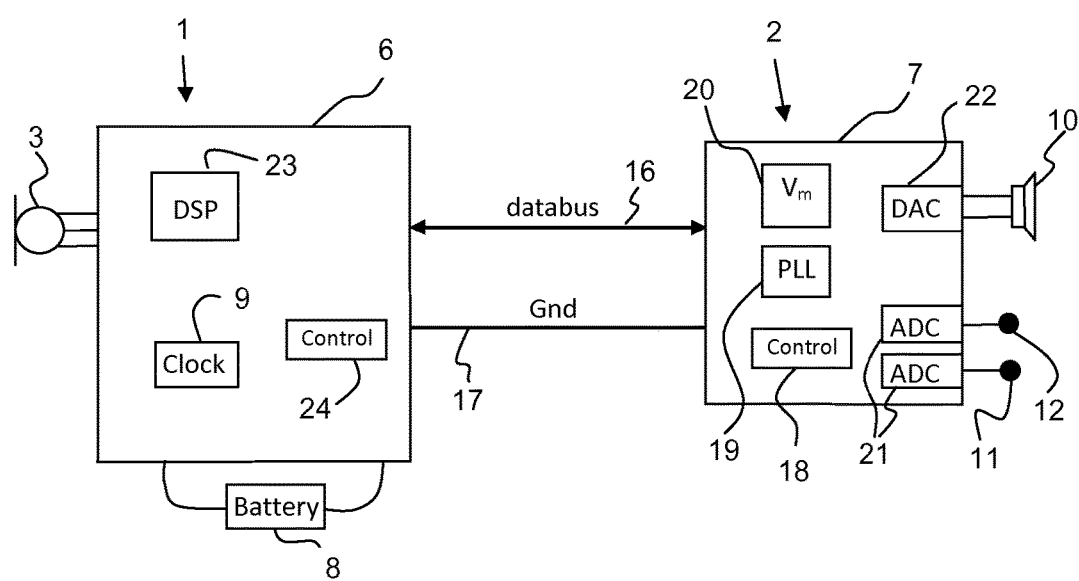
FIG. 1 illustrates an embodiment where an EEG monitor is provided with a databus between the base part and the electrode part.

FIG. 1 shows the principles of an EEG monitor where the base part 1, often arranged behind the ear, comprises an electronic module 6, and a battery 8. The electronic module 6 comprises signal processing means 23, a clock generator 9 and a controller 24 for controlling the communication on the data line or databus 16. The base part may also comprise a microphone 3, which can be applied for building a hearing aid capability into the EEG monitor or for adjusting the sound pressure level of any sounds from the receiver 10 in the electrode part 2 to the background acoustical noise level. Both for FIG. 1 and the following Figs. the description is focused on embodiments where a bidirectional databus is applied, and where a receiver or speaker is arranged in the electrode part.

The electrode part 2 of the EEG monitor comprises an electronic module 7 (i.e. an electronic chip or an integrated circuit) and two or more EEG electrodes 11, 12 for measuring the EEG signal of a person to be monitored. The electrodes are connected with analogue to digital converters 21. The electrode part 2 also comprises a receiver 10.

Figure 2:
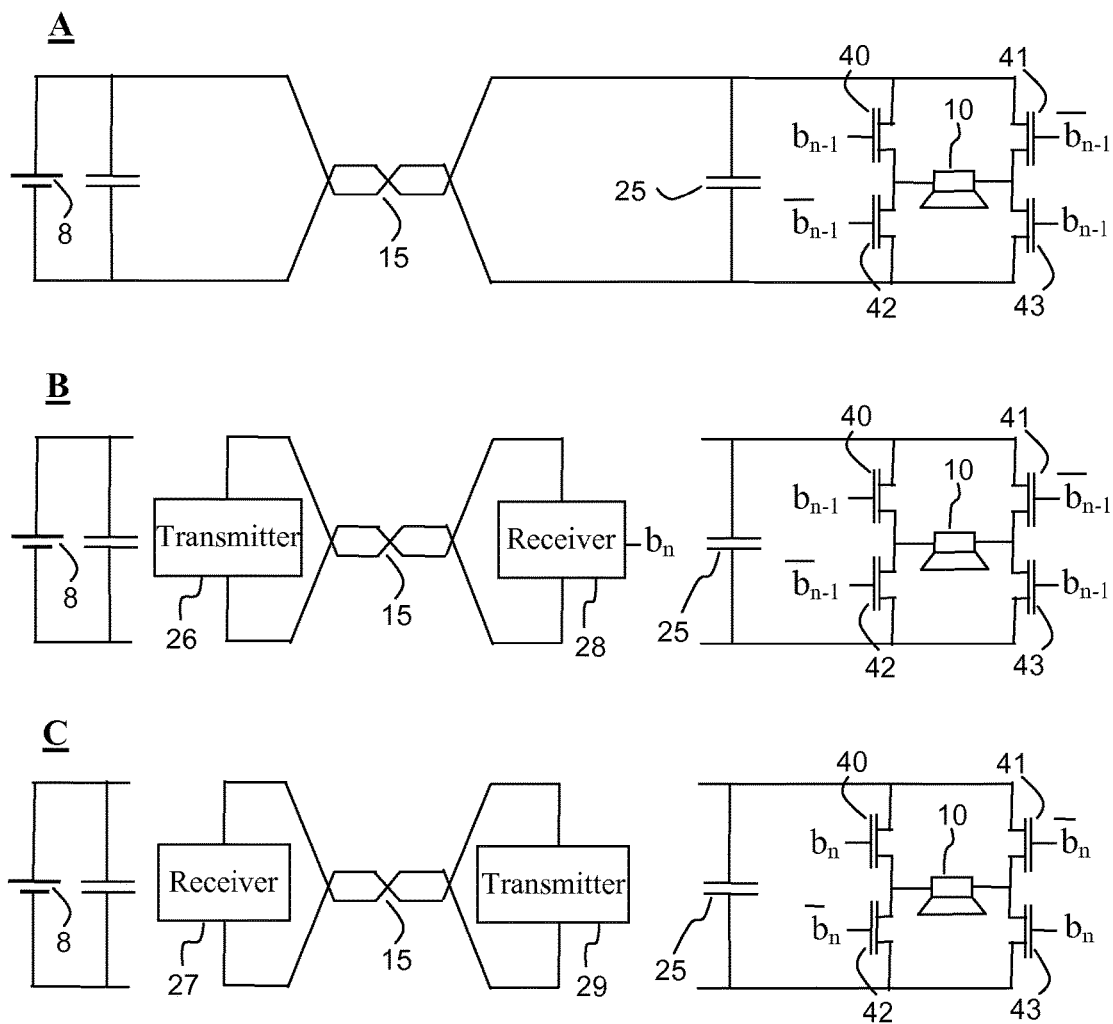
FIG. 2 illustrates the setup of an EEG monitor in three different states of the databus.

The electronic module 7 of the electrode part 2 may comprise a digital to analogue converter 22 for driving the receiver 10, and an analogue to digital converter 21 for digitizing the signal from the EEG electrodes 11, 12 and, e.g., any transducer. The digital to analogue converters may be implemented in the form of delta sigma converters, known from U.S. Pat. No. 5,878,146. A delta sigma converter comprises a delta sigma modulator and a low pass filter. The delta sigma modulator may be arranged in the base part For driving the receiver an H-bridge may be applied. An H-bridge is described in WO-A1-2005/076664 and is also illustrated in FIG. 2.

The receiver 10 in the electrode part may be one single unit handling the whole frequency spectrum of interest. However, the receiver could also be composed of two separate receiver units, one for higher frequencies and one for lower frequencies.

Two electrical wires 16, 17 or lines are connecting the base part with the electrode part in the embodiment illustrated in FIG. 1. The two wires making up the databus are for both the power supply and for the digital communication. A protocol is applied for controlling when power is transmitted and when data is transmitted in either direction on the serial databus. Different types of protocols may be applied for controlling the transmission.

The databus signal may also be sent as a balanced signal on a pair of wires. This will also reduce the risk of noise influencing the databus communication. A balanced pair of wires could be twisted in order to further reduce noise influence.

Usually the battery is arranged in the base part, and a voltage regulator is applied for supplying a stable voltage VDD for the electronic modules. The voltage transferred through the two wires as part of the protocol needs to charge a capacitor from which power is drawn during the data transmission on the databus. Often a local voltage regulator 20 in the electrode part is provided.

FIG. 2 shows an example with three main states A, B and C of the databus. In the first state A the battery 8 in the base part 1 is connected through the databus 15, illustrated as a twisted two electrical wire connection, to the electrode part 2, where the supply voltage will charge the capacitor 25 and power the sound output stage, i.e. the switches 40, 41, 42, 43 in the H-bridge and the receiver 10, e.g. through a voltage regulator. Switches (not shown) in both the base part and in the electrode part are applied for reconnecting the circuit into the B state in FIG. 2. In this state the power supply to the electrode part is disconnected. Instead a transmitter 26 in the base part is connected through the databus 15 to a data receiver 28 in the electrode part. During the B state data is transferred from the transmitter 26 to the data receiver 28. Typically, one bit is transferred during each B state period.

The one or more bit transferred in the B state sets the conditions for the four switches 40, 41, 42, 43 in the H-bridge in the time during other states until a new bit or bits have been transferred in the next B state. The data receiver 28 should be connected to control logic (not shown) for controlling the switches 40, 41, 42, 43 in the H-bridge. The control logic will hold the input to the switches until new data have been received. If more than one bit is transferred to the electrode part in each B state, the control logic should be set up for storing these bits and for presenting the correct bit to the input of the switches 40, 41, 42, 43 at the appropriate time during the time from one B state to the next.

In an example indicated in FIG. 2, $b_n$ is the level of the one bit transmitted to the data receiver 28 in the B state. The level $b_n$ is stored by the control logic, and when shifting from B state to the following C state, the control logic will shift the input on the switches 40, 41, 42, 43 from $b_{n-1}$ to $b_n$. This input $b_n$ will be held until the end of the next B state where it is shifted to $b_{n+1}$. The input $b_{n-1}$ to the switches 40, 41, 42, 43 was transmitted to the data receiver 28 in the B state previous to the one shown in FIG. 2.

As illustrated in FIG. 2 the switches 40, 41, 42, 43 in the H-bridge are switched to be open in one diagonal (e.g. 40 and 43) and close in the other (e.g. 41 and 42). This will open for current through the coil of the receiver in one direction.

When the diagonal where the switches 40, 41, 42, 43 are open changes, the direction of the current, and thereby the movement of the membrane, also changes.

The last state shown in FIG. 2 is the C state following the B state when switches (not shown) in both the base part and in the electrode part are applied for reconnecting the circuit into the C state. In the C state a transmitter 29 in the electrode part 2 transmits one or more bits through the databus 15 to a data receiver 27 in the base part. These data transmitted out of the electrode part is the digitized EEG signal. Data from any further transducer will be digitized by an A/D converter 21 and packed for transmission in a control unit 18 in the electrode part.

A further D state where a low bit or a "0" is sent on the databus is often following the C state, in order to initiate the A state with a rising edge. Such a rising edge is used for synchronization between the base part and the electrode part as described below.

The capacitor 25 will be the power source to the receiver 10, H-bridge and other power demanding circuits in the electrode part during the B, C and D states where no power, but only data, is transferred through the databus 15. The voltage regulator 20 (see FIG. 1) will ensure that the correct voltage is provided in all states. The databus 15 will thus face a relatively low impedance in the A state. In the B state the transmitter 26 will have low output impedance whereas the data receiver 28 will have high impedance. In the C state the transmitter 29 will have low output impedance whereas the data receiver 27 will have high input impedance.

In practice the capacitor 25 may be implemented as two capacitors in parallel (not shown). This would facilitate that one of these two capacitors could be applied for providing power supply to the H-bridge in the B and C state, and the other one of these two capacitors could be applied for providing power supply to either the data receiver 28 in the B state or to the transmitter 29 in the C state.

In an embodiment where the receiver 10 or speaker is connected such that it will not draw any power in the time where data is transferred on the databus, but only in the time where power is transferred, the four switches 40, 41, 42, 43 in the H-bridge should be operated differently. The control logic controlling the switches 40, 41, 42, 43 in the H-bridge will then hold the input to the switches as described above only in the state where power is transferred, i.e. state A in the example. In the other states the receiver 10 could be short circuited in order not to draw any power from the capacitor 25. Short circuiting the receiver 10 may be achieved by opening switches 40, 41 simultaneously and closing switches 42, 43 simultaneously. It could also be opposite, i.e. closing switches 40, 41 and opening switches 42, 43.

Figure 3:
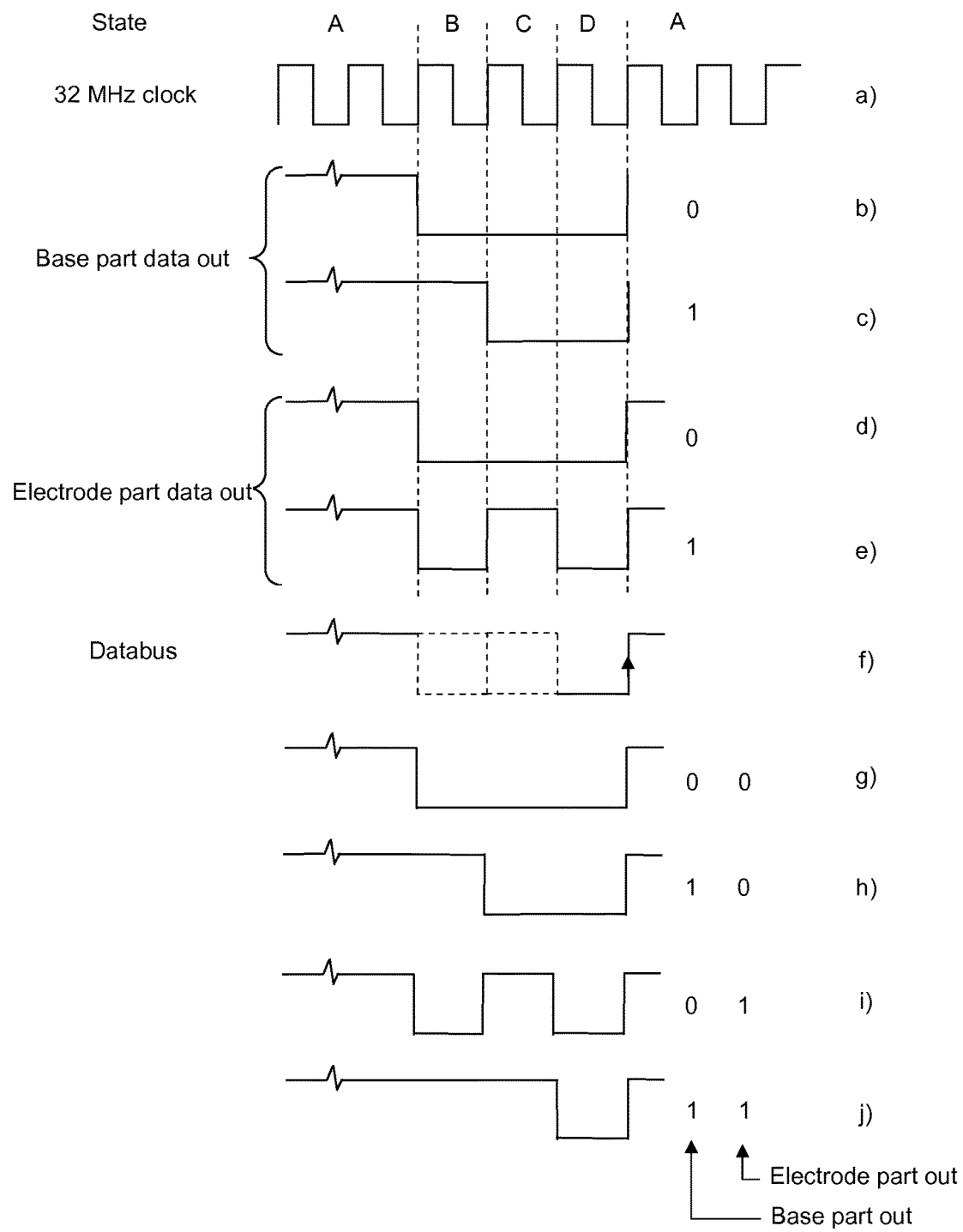
FIG. 3 illustrates the bidirectional digital communication through a databus, panes (a) through (j) signifying respective signals.
Figure 4:
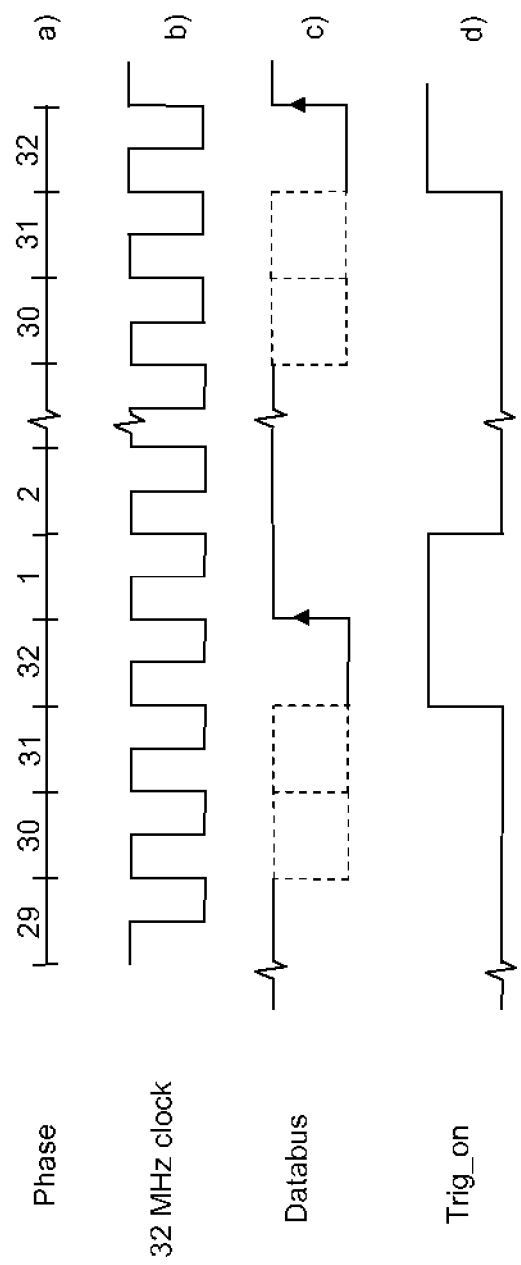
FIG. 4 illustrates different states for controlling the bidirectional digital communication, panes (a) through (d) signifying respective signals.

FIGS. 3 and 4 shows one example on how the power supply and the communication through a two wire bidirectional serial databus 16 could be handled. In FIG. 3 pane a, a 32 MHz clock frequency generated in the base part 1 is shown. A corresponding 32 MHz clock frequency is generated in the electrode part 2 by application of a phase-locked loop (PLL) circuit 19 (see FIG. 5). The PLL 19 regenerates the 32 MHz clock frequency by application of the databus signal. The PLL continuously adjusts the synchronization between the two 32 MHz clock frequencies, by application of rising edges in the data line signal. When the clock generator 9 is arranged in the base part, as in this example, the PLL is arranged in the electrode part. This synchronization is important for the proper functioning of the communication between the base part 1 and the electrode part 2.

The 32 MHz clock frequency is to be regarded as an example. Also other clock frequencies can be applied.

As illustrated in FIG. 3 pane a, the 32 MHz clock cycles can be divided into four different states (see top of FIG. 3) called A, B, C and D. In state A power is transferred, preferably from the base part to the electrode part. In state B data is transferred from the base part to the electrode part. This would typically be the electrical signal to the receiver for the receiver to generate the acoustic signal. In state C data is transferred from the electrode part to the base part. Such data is the digitized signal from the EEG electrodes and maybe other transducers in the electrode part. The state D is always low or "0" such that the state A will start with a rising edge. This gives a rising edge for every cycle where the rising edges have a well defined time interval. These rising edges are then applied for synchronization of the clock frequency between the base part and the electrode part. The order of the suggested states may be different. The state A could also be divided into two, or more, parts, separated by interchanging B and C states. It is also possible to add further states with other purposes in between the described states.

FIG. 3 panes b and c show an example on sending one bit from the base part to the electrode part, where a "0" is sent in FIG. 3 pane b and a "1" is sent in FIG. 3 pane c. In both FIG. 3 pane b and in FIG. 3 pane c, a "0" is sent out of the electrode part.

FIG. 3 panes d and e show an example on sending one bit from the electrode part to the base part, where a "0" is sent in pane d and a "1" is sent in pane e. In both FIG. 3 panes d and e, a "0" is sent out of the base part.

FIG. 3 pane f shows the resulting signal on the bidirectional databus, where the dashed lines indicate that the signal can follow one of the two possible routes, resulting in either a "0" or a "1" being sent. This resulting signal on the databus is a summation of signals from FIG. 3 pane b or c, and FIG. 3 pane d or e. In the example there will be a rising edge, indicated by an arrow in FIG. 3 pane f, in the databus signal for every 32 rising edges in the 32 MHz clock frequency. This means that the signal on the databus must go low before this rising edge, which is also the case in the databus signal shown in FIG. 3 pane f, due to the D state. A change in the databus signal level only occurs on rising edges of the 32 MHz clock frequency.

The mentioned rising edges in the data line signal, indicated with an arrow in FIG. 3 pane f, are applied for the PLL to synchronize the clock signals between the base part and the electrode part.

FIG. 4 shows signals applied in the synchronization of the clock frequency. FIG. 4 pane a further illustrates the counting of phases by a phase counter. A phase counter is present in both the base part and in the electrode part. The phase counter is part of a control means 18 of the electrode part. The two phase counters are synchronized by the PLL via rising edges on the databus. The phase counter starts on 1 on a rising edge of the databus signal and increments by one for each rising edge on the 32 MHz clock until 32. After 32 the phase counter starts from 1 again. The phase counters could also be incremented by half by identifying the falling edges on the 32 MHz clock.

The phase counters are applied for identifying the states A where power is to be transferred, and the states B and C where either the base part or the electrode part is sending data out.

FIG. 4 pane b repeats the 32 MHz clock frequency, and FIG. 4 pane c repeats the databus signal, both for ease of comparison in FIG. 4. It is seen from FIGS. 3 and 4 that the state A is active in the phase 1-29, the state B is active in the phase 30, the state C is active in the phase 31 and the state D, where a "0" is transmitted, is active in the phase 32. The phase count is also applied for shifting between the different setups illustrated in FIG. 2 for the different states. The different phases with the different states are regarded as different time slots.

The rising edge between the state D and the state A is intended for synchronization of the clock frequency in the base part and in the electrode part. This rising edge is illustrated with arrows in FIG. 3 pane f and in FIG. 4 pane c. A different rising edge will occur between state B and C every time a "0" is sent out by the base part followed by a "1" sent out by the electrode part. In order to discriminate between these two rising edges, the control unit 18 of the electronic module 7 of the electrode part 2 is arranged for generating a signal to be applied for this discrimination. This signal is called Trig_on and is illustrated in FIG. 4 pane d.

The Trig_on signal is set to "1" (or high), when the phase equals 32 or 1. The Trig_on signal is set to "0" (or low), when the phase is from 2 to 31. At least Trig_on should be low in phase 30 and 31.

Figure 5:
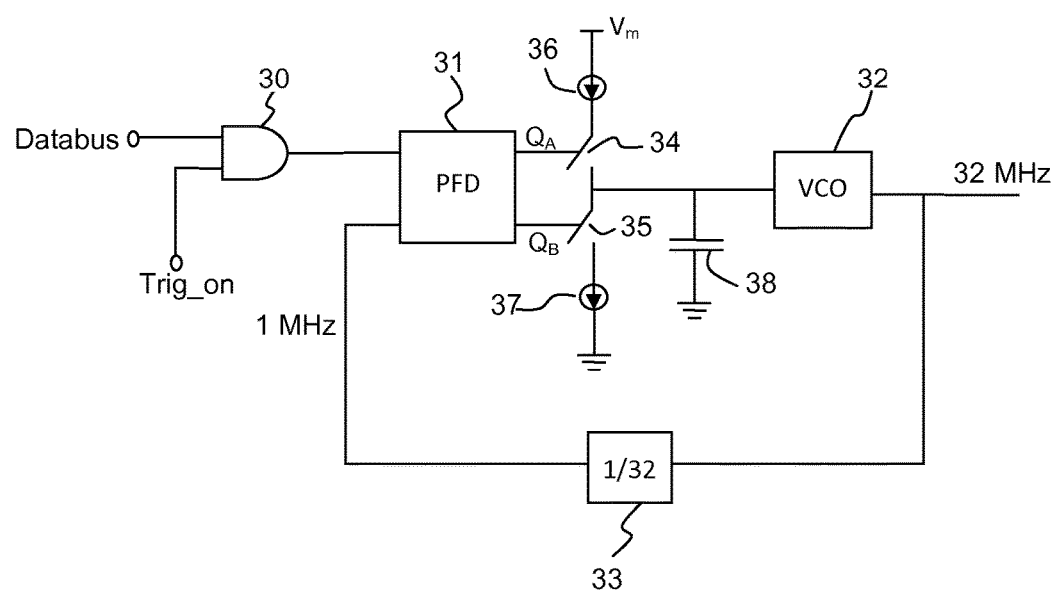
FIG. 5 illustrates a phase locked loop circuit applied in an embodiment of the invention.

FIG. 5 shows an example of the phase locked loop (PLL) circuit 19 applied for synchronizing the 32 MHz clock frequency between the base part and the electrode part by application of rising edges marked with arrows in FIG. 3 pane f and FIG. 4 pane c. The data line signal goes to an AND operator 30 together with the Trig_on signal. The output of the AND operator 30 will thus only go high for the rising edges of the data line signal, marked with an arrow, and not for the rising edge when a "0" is sent out of the base part followed by a "1" sent out of the electrode part (see FIG. 4 pane c and d). This is because the Trig_on signal is high at the data line rising edge marked with an arrow, while it is low when sending signal bits out of the base part or out of the electrode part.

The signal from the AND operator 30 is the reference input to the phase frequency detector (PFD) 31. The other input to the PFD 31 is the feedback from the voltage controlled oscillator (VCO) 32 through a divider 33. The two outputs QA and QB of the PFD 31 control a first switch 34 and a second switch 35 through a train of pulses. A first constant current generator 36 and a second constant current generator 37 will either charge or discharge a capacitor 38, thereby determining the input voltage to the VCO 32. The two current generators 36, 37 usually generate the same current. A pulse on QA will close the first switch 34 connected with QA, whereby the first constant current generator 36 will be charging the capacitor 38. A pulse on QB will close the second switch 35 connected with QB, whereby the second constant current generator 37 will be discharging the capacitor 38.

When the two signals on the inputs of the PFD 31 are synchronized or locked, the length of the pulses QA and QB are the same and the voltage on the VCO 32 input remains unchanged. If the two signals on the inputs of the PFD 31 are out of synchronization, the pulses on one of the outputs QA and QB of the PFD 31 become longer than the pulses on the other output, thereby either charging or discharging the capacitor 38. This will adjust the input voltage on the VCO 32 to a level where the output frequency of the VCO is synchronized with the databus signal.

When starting up the databus, especially in the example of the bidirectional databus, e.g. when turning on the EEG monitor, or when resetting the databus, the controller 18 should wait for the PLL to lock, i.e. for the two 32 MHZ frequencies to become synchronized. This is the case when the lengths of the pulses QA and QB are the same or approximately the same. When this happens, the electrode part will be waiting for a rising edge on the data line. When the controller 18 detects a rising edge on the data line, the phase counter is set to 1. From this point in time the phase counter will continue as shown in FIG. 4 pane a, and as described above. In order for this start up procedure to function properly, the situation in FIG. 3 pane i should be avoided, i.e. a "0" from the base part followed by a "1" from the electrode part should be avoided during start up in order not to get any other rising edge which could disturb the synchronization. This means that the databus signal initially has to look like the signal in FIG. 3 panes g, h or j.

Resetting the databus, and subsequent application of the above start-up procedure, can be initialized if the connection at one or more lines or wires is temporarily lost. Such a temporary loss of connection can be detected by the control circuit 18 of the electronic module 7 in the electrode part. This could be done by checking the voltage over the capacitor 38 in the PLL 19 (see FIG. 5). The rising edges of the databus signal stops, this voltage will fall towards zero, and when the control circuit 18 detects this, the electrode part should stop sending data on the databus, and at the same time the above start-up procedure should be initialized. The control circuit 18 may also be set up for detecting any temporary loss of connection on the power supply wires.

A specific code may be applied for confirming that the clock frequencies are properly synchronized. This code, or a different code, could also be sent with specific time intervals to confirm that the communication is functioning as scheduled. If this code stops, or the time intervals are not properly followed, a reset procedure could also be initialized. Such code will need to be sent as part of the signals sent out of the base part or out of the electrode part arranged at specific times in the sequence of data signals.

In the above example of the data communication, one cycle of the clock frequency is applied for sending one bit from the base part to the electrode part and one bit from the electrode part to the base part. The data communication could be arranged in many other ways. Other options within the embodiments of the invention could be to send e.g. 2 or 4 bits from the base part followed by the same, or a different, number of bits sent from the electrode part to the base part. The advantage of only sending one bit at a time is that the capacitor needed in the electrode part for holding the supply voltage can be relatively smaller since the time in which the supply voltage needs to be held, without the capacitor receiving extra charge, will be relatively shorter. The number of bits sent in each of the two directions does not have to be the same. This could depend on the needs of the databus and the one or more transducers in the electrode part.

Also the clock frequency will influence the necessary size of the capacitor. With a 32 MHz clock frequency, power will be transferred in the fraction $29/32$ of time according to the example above where data is sent out of the base part at 1 Mbit/s and data is sent out of the electrode part at 1 Mbit/s. This means that the capacitor 25 only needs to hold the supply voltage in $3/32$ of a microsecond. If the clock frequency was 4 MHz and the demands for data transfer were the same, the capacitor would need to hold the supply voltage for $3/4$ of a microsecond. At the same time power would only be transferred in the fraction $1/4$ of time. This means that the capacitor should be larger and that the current running through the databus while transferring power would need to be higher in order to supply the necessary charge.

A higher current during the power supply period, i.e. state A, will lead to a higher power loss compared to the power loss at a lower current.

When the time fraction where no power is transferred is increased, the size of the capacitor 25 needs to be increased, in order for the capacitor to hold enough charge to be able to supply power in the time without power supply. Larger capacity also means physical larger dimensions of the capacitor. Due to the need for a small electrode part, a small capacitor, and thus a relatively high clock frequency will often be preferred.

A higher frequency will, however, also lead to a higher dynamic efficiency loss in the p-n junctions of the control circuit. This power loss is caused by charging the capacitive load of logic gates. For the databus alone the actual frequency causing this power loss is lower than the clock frequency, since the databus will be on the same level during the cycles of the A state. The number of shifts between "0" and "1" will therefore often be considerably lower than the controlling clock frequency, i.e. 32 MHz in the example. Thereby, the dynamic efficiency loss is also reduced.

1 Mbit/s should be sufficient for supplying the receiver 10 with an electrical sound signal of the necessary quality. For electrodes 11, 12 in the electrode part 2 the signal is digitized by A/D converters 21 and this may result in a signal of less than around 2 Mbit/s. The EEG signals, which may comprise several inputs from different electrodes, will usually be pre-processed in the electrode part and thereby reduced to approximately 600 kbit/s or less. Signals from other transducers in the electrode part will also be pre-processed and transferred as part of this signal. A signal at this rate can easily be transmitted through the databus of the above example. The preprocessing is a decimation of the signal by a reduction of the sampling frequency and a low pas filtering, whereby high frequency, quantification noise is removed.

In the embodiment where the receiver 10 or speaker is connected such that it will not draw any power in the time where data is transferred on the databus, but only in the time where power is transferred, the maximum acoustic output power from the receiver 10 will be reduced slightly. In the example with a 32 MHz clock frequency where power is transferred in the fraction $^{29}/_{32}$ of the time the reduction in maximum acoustic output power from the receiver 10 will be $^{3}/_{32}$ or approximately 1 dB.

When adding further transducers to the electrode part, where data needs to be transferred through the databus to the base part, further bandwidth of the databus is necessary. Depending on the type of these transducers the amount of data to transfer may vary significantly. If the transducer is a thermometer or an accelerometer for detection of movements, the necessary amount of data for transfer may be relatively limited, whereas when the transducer is a microphone more data need to be transferred.

When a number of transducers are comprised in or connected with the electrode part, the data from these may be collected by the electronic module 7 of the electrode part and packaged into a format suitable for sending via the databus together with the digitized EEG signal.

Figure 6:
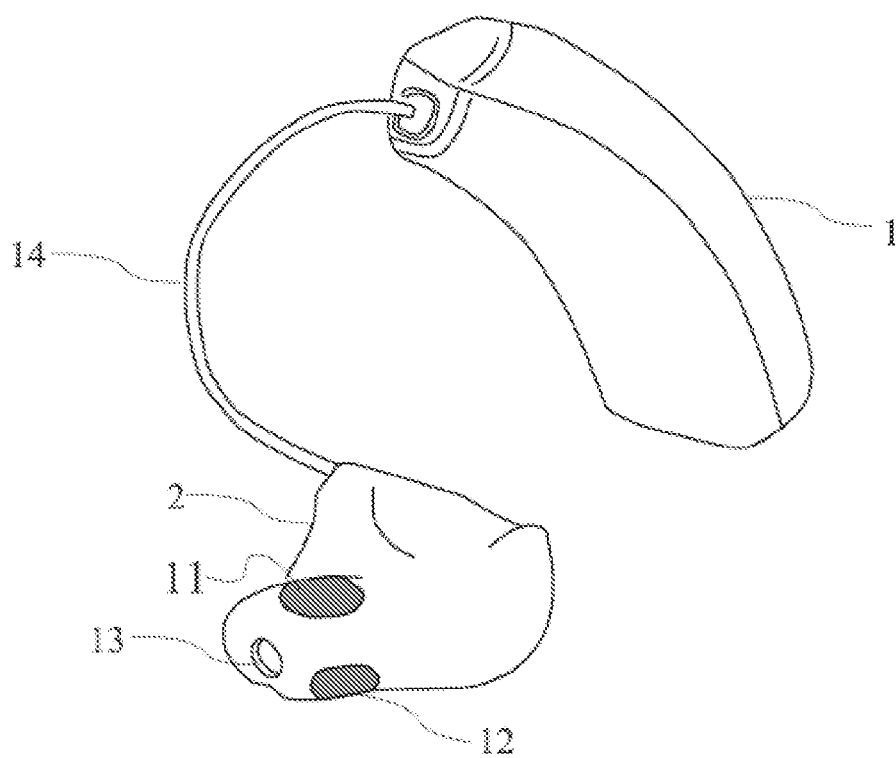
FIG. 6 illustrates an example of a mechanical layout of an EEG monitor.

FIG. 6 shows an example of an EEG monitor with the base part 1 prepared to be arranged behind the ear with the electrode part 2 prepared to be arranged in the ear canal of the person who needs to have the EEG signal monitored. The base part and the electrode part are connected by two electrical wires 14. The electrode part 2 is here illustrated as having two electrodes 11, 12, but will often have more electrodes, e.g. three, four or five. With a higher number of electrodes it may be possible to select the EEG signal from those electrodes having the best contact or for other reasons receiving the best EEG signal. Also differences in the EEG signal between different sets of electrodes may be applied in the analysis of the EEG signal.

The electrode part is formed as an ear plug shaped to fit the ear canal of the person who needs to wear the EEG monitor. By shaping the ear plug to the ear canal of the individual, the electrode part will be less annoying to wear, and it is ensured that the electrodes will always be placed at the same spot in the ear canal.

The electrode part will usually be provided with a through going opening 13 in order for sound to pass into the ear canal without being obstructed. The speaker arranged in the ear plug may apply this opening 13 or a different opening for supplying sound into the inner part of the ear canal.

The electrodes 11, 12 illustrated in FIG. 6 may be of any type, e.g. being based on obtaining an electrical connection to the skin or being of the capacitive type where no electrical connection is obtained, but the EEG signal is measured through a capacitive coupling to the skin surface.

We claim:

1. A personal EEG monitor, comprising a base part having a signal processor, an electrode part with at least two electrodes for measuring an EEG signal of a person, said electrode part having an analog-to-digital converter for converting the EEG signal into a digital signal, and a two-wire databus for transferring data between said base part and said electrode part over two wires with said base part and electrode part located adjacent one ear, and for providing power over said two wires from one part to the other; and for the application of at least four different states in respective time slots, where a first state is during a first period of time and is for transfer of power, a second state is during a second period of time and is for transmission of signal from said base part to said electrode part, a third state is during a third period of time and is for transmission of signal from said electrode part to said base part; and a fourth state is during a fourth period of time and is set to low in order for the first state to start with a rising edge, with no power being transferred between said base part and electrode part during said second and third states, and wherein data to be transferred includes at least first and second values, and said databus represents said first value with a first signal level and represents said second value with a second signal level.

2. A personal EEG monitor, comprising
   a base part having a signal processor,
   an electrode part with at least two electrodes for measuring an EEG signal of a person, said electrode part having an analog-to-digital converter for converting the EEG signal into a digital signal, and
   a two-wire databus for transferring data between said base part and said electrode part over two electrical wires with said base part and electrode part located adjacent one ear, and for also providing power from one part to the other over said two wires, wherein data to be transferred includes at least first and second values, and said databus represents said first value with a first signal level and represents said second value with a second signal level different from the first signal level.

3. The EEG monitor according to claim 2, wherein two different states of the databus are applied in different time slots, including at least a first state for transfer of power without transfer of data, and a second state for transmission of signal from said electrode part to said base part without transfer of power.

4. The EEG monitor according to claim 3, wherein said databus is configured such that said first state for transfer of power takes up at least 50% of the time on the databus.

5. The EEG monitor according to claim 4, wherein said first state for transfer of power takes up at least 70% of the time on the databus.

6. The EEG monitor according to claim 2, wherein at least three different states of the databus are applied in different time slots, where a first state is for transfer of power, a second state is for transmission of signal from said base part to said electrode part without transfer of power, and a third state is for transmission of signal from said electrode part to said base part without transfer of power.

7. The EEG monitor according to claim 2, wherein said electrode part includes a capacitor charged during said first state and for supplying power to components of said electrode part during said second and third states, said components including a receiver which is powered from said two-wire databus and not from said capacitor.

8. The EEG monitor according to claim 6, wherein said electrode part includes a receiver, and wherein supply of power to said receiver is disconnected during at least one of said second and third states.

9. The EEG monitor according to claim 2, wherein a power supply is arranged in said base part and a capacitor is arranged in said electrode part, said capacitor being adapted for being charged during a first state for transfer of power, and for supplying power in periods where no power is transmitted through the databus.

10. The EEG monitor according to claim 9, wherein said electrode part comprises a receiver for providing a sound signal to said person.

11. The EEG monitor according to claim 10, wherein said receiver is connected such that it will not draw any power in the time where data is transferred on the databus.

12. The EEG monitor according to claim 2, wherein said electrode part is adapted to be arranged in the ear canal of the person to be monitored.

13. The EEG monitor according to claim 2, wherein said electrode part comprises an electronic chip connected with the at least two electrodes, said electronic chip being connected with said databus.

14. The EEG monitor according to claim 13, wherein said electronic chip comprises a power supply and a voltage regulator for the power supply.

15. The EEG monitor according to claim 13, wherein said analog-to-digital converter is located on said electronic chip.

16. The EEG monitor according to claim 15, wherein said analog-to-digital converter is a sigma-delta converter.

17. The EEG monitor according to claim 2, comprising a clock frequency generator arranged in either the base part or in the electrode part of the EEG monitor, and a clock frequency regenerator in the part of the EEG monitor without the clock frequency generator.

18. The EEG monitor according to claim 17, wherein said clock frequency regenerator is synchronized with the clock frequency of said clock frequency generator.

19. The EEG monitor according to claim 18, comprising a phase-locked loop for synchronizing the clock frequency regenerator.

20. The EEG monitor according to claim 17, wherein said clock frequency generator is arranged in said base part of the EEG monitor.

21. The EEG monitor according to claim 2, wherein the electrode part is adapted to be arranged in the ear canal of the one ear of the person to be monitored and comprises a receiver, and said EEG monitor comprises sound amplification means and at least one microphone.

22. The EEG monitor of claim 2, wherein said two wires are used for transmission of data from said base part to said electrode part and from said electrode part to said base part, and for transfer of power.

23. The EEG monitor according to claim 2, wherein said two-wire data bus transfers power between said base part and said electrode part during a time when no data is being transferred between said base part and electrode part.

24. The EEG monitor according to claim 2, wherein each of said two wires provides an unbroken electrical path between said base part and electrode part.

25. The EEG monitor according to claim 2, wherein there is no electrical connection between said base part and electrode part that does not pass through said two wires.

26. A method for operating the EEG monitor of claim 2, comprising the steps of:
arranging said base part outside the ear canal of the one ear,
arranging said electrode part in the ear canal of the person, and
connecting said electrode part with said base part through said databus.

27. The method according to claim 26, further comprising a step of applying at least two different states of the two wire databus sequentially in different time spans, where a first state is for transfer of power, and a second state is for transmission of signal from said electrode part to said base part.

28. The method according to claim 26, comprising applying at least three different states of the two wire databus sequentially in different time spans, where a first state is for transfer of power, a second state is for transmission of signal from said base part to said electrode part, and a third state is for transmission of signal from said electrode part to said base part.

* * * * *